(12) United States Patent
Takei (10) Patent No.: US 12,272,049 B2
(45) Date of Patent: Apr. 8, 2025

(54) LEARNING DEVICE, METHOD, AND PROGRAM, MEDICAL IMAGE PROCESSING APPARATUS, METHOD, AND PROGRAM, AND DISCRIMINATOR

(71) Applicant: FUJIFILM Corporation, Tokyo (JP)

(72) Inventor: Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 532 days.

(21) Appl. No.: 17/553,641

(22) Filed: Dec. 16, 2021

(65) Prior Publication Data

US 2022/0108451 A1    Apr. 7, 2022

Related U.S. Application Data

(63) Continuation of application No. PCT/JP2020/025399, filed on Jun. 26, 2020.

(30) Foreign Application Priority Data

Jun. 28, 2019    (JP) ................................. 2019-121015

(51) Int. Cl.
*G06T 7/00* (2017.01)
*A61B 6/50* (2024.01)
(Continued)

(52) U.S. Cl.
CPC .............. *G06T 7/0012* (2013.01); *G06N 3/08* (2013.01); *G06V 10/7747* (2022.01);
(Continued)

(58) Field of Classification Search
CPC ......... G06T 7/0012; G06T 2207/20081; G06T 2207/30016; G06N 3/08; G06V 10/7747; G06V 2201/031; G16H 30/40
See application file for complete search history.

(56) References Cited

U.S. PATENT DOCUMENTS 11,207,045 B2    12/2021  Sankaran et al.
11,830,195 B2 *  11/2023  Takahashi ............. G06F 18/214
(Continued)

FOREIGN PATENT DOCUMENTS

JP    2018061771    4/2018
JP    2019509813    4/2019

OTHER PUBLICATIONS

Yuki Shimabara, "Development of cerebral aneurysm detection software utilizing deep learning," with partial English translation thereof, Medical Imaging and Information Sciences, vol. 34, No. 2, 2017, pp. 1-3.

(Continued)

*Primary Examiner* — Matthew C Bella
*Assistant Examiner* — Janice E. Vaz
(74) *Attorney, Agent, or Firm* — JCIPRNET (57) ABSTRACT

An information acquisition unit acquires a learning image including a disease region and a first teacher label that specifies the disease region included in the learning image. A teacher label generation unit generates at least one second teacher label of which a criterion for specifying the disease region is different from the first teacher label. A learning unit trains a discriminator that detects a disease region included in a target image on the basis of the learning image, the first teacher label, and the at least one second teacher label.

12 Claims, 11 Drawing Sheets

(51) Int. Cl.
*G06N 3/08* (2023.01)
*G06V 10/774* (2022.01)
*G16H 30/40* (2018.01)

(52) U.S. Cl.
CPC .............. *G16H 30/40* (2018.01); *A61B 6/501* (2013.01); *G06T 2207/10081* (2013.01); *G06T 2207/10088* (2013.01); *G06T 2207/10104* (2013.01); *G06T 2207/20081* (2013.01); *G06T 2207/20084* (2013.01); *G06T 2207/30016* (2013.01); *G06V 2201/031* (2022.01)

(56) References Cited

U.S. PATENT DOCUMENTS

| | | | |
|---|---|---|---|
| 2017/0265831 A1 | 9/2017 | Sankaran et al. | |
| 2019/0192096 A1 | 6/2019 | Wu et al. | |
| 2020/0027561 A1* | 1/2020 | Rao | A61B 5/0042 |
| 2020/0342257 A1* | 10/2020 | Ichinose | G06T 7/0012 |
| 2021/0272284 A1* | 9/2021 | Kamiyama | G06N 20/20 |
| 2021/0272288 A1* | 9/2021 | Takahashi | G06F 18/214 |
| 2022/0148323 A1* | 5/2022 | Watanabe | G06T 11/00 |

OTHER PUBLICATIONS

Nagarajan Natarajan et al., "Leaning with Noisy Labels," NIPS'13: Proceedings of the 26th International Conference on Neural Information Processing Systems, vol. 1, 2013, pp. 1196-1204.

Jiangfan Han et al., "Deep Self-Learning From Noisy Labels," arXiv:1908.02160vl, Aug. 2019, pp. 1-10.

"International Search Report (Form PCT/ISA/210) of PCT/JP2020/025399," mailed on Sep. 1, 2020, with English translation thereof, pp. 1-6.

"Written Opinion of the International Searching Authority (Form PCT/ISA/237)" of PCT/JP2020/025399, mailed on Sep. 1, 2020, with English translation thereof, pp. 1-6.

* cited by examiner

FIG. 11

LEARNING DEVICE, METHOD, AND PROGRAM, MEDICAL IMAGE PROCESSING APPARATUS, METHOD, AND PROGRAM, AND DISCRIMINATOR

CROSS REFERENCE TO RELATED APPLICATIONS

The present application is a Continuation of PCT International Application No. PCT/JP2020/025399, filed on Jun. 26, 2020, which claims priority to Japanese Patent Application No. 2019-121015, filed on Jun. 28, 2019. Each application above is hereby expressly incorporated by reference, in its entirety, into the present application.

BACKGROUND

Technical Field

The present disclosure relates to a learning device, a learning method, and a learning program which trains a discriminator for extracting a disease region included in a medical image, a medical image processing apparatus, a medical image processing method, and a medical image processing program which use a trained discriminator, and a discriminator constructed by learning.

Related Art

In recent years, with advances in medical equipment such as computed tomography (CT) devices and magnetic resonance imaging (MRI) devices, an image diagnosis using high resolution medical images having higher quality can be performed. In particular, in a case where a target part is a brain, since it is possible to specify a disease region causing vascular disorders such as cerebral infarction and cerebral hemorrhage, by the image diagnosis using CT images and Mill images, an appropriate treatment can be performed on the basis of the specified result. In general, the disease region shows a higher or lower CT value on the CT image as compared with the surrounding region. Therefore, it is possible to discriminate a disease region by interpreting the presence or absence of a region showing a higher or lower CT value as compared with the surrounding region in the image diagnosis.

Further, in order to reduce the burden on doctors who interpret images, the medical image is analyzed by a computer-aided diagnosis (CAD) using a discriminator consisting of neural networks and the like in which machine learning has been performed by deep learning or the like to detect a disease region such as a bleeding region and an infarction region in the brain.

Here, in a case of training the discriminator used in the above-described CAD, teacher data that includes learning images including a disease region, and a teacher label specifying the disease region by labeling the disease region in the learning image is prepared in advance. Assigning the labels to the disease regions of the learning images is performed manually by the doctor. In a case of training the discriminator, the learning images are input to the discriminator, the disease region in the learning image is detected, the difference between the detection result and the teacher label is derived as a loss, and the discriminator is trained using the derived loss.

On the other hand, in a case of training the discriminator, various methods have been proposed for adjusting a shape detection accuracy according to a doctor's desire. For example, in JP2018-061771A, a method has been proposed which extracts a feature quantity of a disease region using learning parameters obtained by training the discriminator, adds types of feature labels relating to the disease region according to the feature label newly added by the user's input, and updates the learning parameters. Further, JP2018-061771A has also proposed to perform machine learning by adding the feature labels.

In a case where the medical image is a non-contrast CT image, in mild subarachnoid hemorrhage or cerebral infarction in the hyperacute phase, the contrast between the part where the disease is occurring and the surrounding part is unclear in many cases. In such a case, it is difficult to accurately perform the labeling of the disease region. Further, in a case where the contrast between the part where the disease is occurring and the surrounding part is unclear, the region to be determined as the disease region differs depending on the doctor performing the labeling, in many cases. For example, in a case where a doctor watches the disease region labeled by another doctor, a region wider than the labeled region may be determined as the disease region. In such a case, since a region that may be detected is learned as a region that should not be detected in a case where the discriminator is trained using a narrowly labeled disease region as a teacher label, there is a possibility that the disease region is overlooked.

In the method disclosed in JP2018-061771A, a size of the disease region can be added as a feature label. However, in the method disclosed in JP2018-061771A, the feature label is added by the doctor's input. Thus, the problem of overlooking the disease region due to the fact that the region to be determined as the disease region differs depending on the doctor is not solved.

SUMMARY OF THE INVENTION

The present disclosure is made in view of such circumstances, and an object thereof is to prevent the overlooking of the disease region.

A learning device according to an aspect of the present disclosure comprises an information acquisition unit that acquires a learning image including a disease region and a first teacher label that specifies the disease region included in the learning image; a teacher label generation unit that generates at least one second teacher label of which a criterion for specifying the disease region is different from the first teacher label; and a learning unit that trains a discriminator that detects a disease region included in a target image on the basis of the learning image, the first teacher label, and the at least one second teacher label.

In the learning device according to the aspect of the present disclosure, the teacher label generation unit may generate the at least one second teacher label using the first teacher label.

In the learning device according to the aspect of the present disclosure, the teacher label generation unit may generate the at least one second teacher label on the basis of a distribution of signal values of a region in the first teacher label and a position of the first teacher label in the learning image.

In the learning device according to the aspect of the present disclosure, the teacher label generation unit may derive a representative value of the signal values in the region of the first teacher label in the learning image, and generate a region corresponding to the first teacher label and a region in which signal values of a region adjacent to the region in the first teacher label in the learning image are within a predetermined range with respect to the representative value, as the second teacher label.

As the "representative value", for example, an average value, a weighted average value, a median, a maximum value, a minimum value, or the like can be used.

In the learning device according to the aspect of the present disclosure, the learning unit may train the discriminator by inputting the learning image to the discriminator to detect a learning disease region, deriving a first loss between the learning disease region and the first teacher label and a second loss between the learning disease region and the second teacher label, deriving a total loss from the first loss and the second loss, and using the total loss in training the discriminator.

In the learning device according to the aspect of the present disclosure, the learning image may include a brain, and the disease region may be a region of a brain disease.

A medical image processing apparatus according to another aspect of the present disclosure comprises a disease region detection unit to which the discriminator trained by the learning device according to the aspect of the present disclosure is applied, and which detects a disease region included in a target medical image in a case where the target medical image is input.

The medical image processing apparatus according to the aspect of the present disclosure may further comprise a labeling unit that performs labeling of the disease region detected from the target medical image; and a display control unit that causes a display unit to display the labeled target medical image.

A discriminator according to another aspect of the present disclosure is trained by the learning device according to the aspect of the present disclosure, and detects a disease region included in a target medical image in a case where the target medical image is input.

A learning method according to another aspect of the present disclosure comprises acquiring a learning image including a disease region and a first teacher label that specifies the disease region included in the learning image; generating at least one second teacher label of which a criterion for specifying the disease region is different from the first teacher label; and training a discriminator that detects a disease region included in a target image on the basis of the learning image, the first teacher label, and the at least one second teacher label.

A medical image processing method according to another aspect of the present disclosure detects a disease region included in a target medical image in a case where the target medical image is input, using the discriminator trained by the learning method according to the aspect of the present disclosure.

A program for causing a computer to execute the learning method and the medical image processing method according to the aspect of the present disclosure may be provided.

A learning device according to another aspect of the present disclosure comprises a memory that stores a command for execution of a computer; and a processor configured to execute the stored command, and the processor acquires a learning image including a disease region and a first teacher label that specifies the disease region included in the learning image, generates at least one second teacher label of which a criterion for specifying the disease region is different from the first teacher label, and trains a discriminator that detects a disease region included in a target image on the basis of the learning image, the first teacher label, and the at least one second teacher label.

A medical image processing apparatus according to another aspect of the present disclosure comprises a memory that stores a command for execution of a computer; and a processor configured to execute the stored command, and the processor executes a process of detecting a disease region included in a target medical image in a case where the target medical image is input, using the discriminator trained by the learning method according to the aspect of the present disclosure.

According to the present disclosure, it is possible to prevent the overlooking of the disease region included in the target image.

DETAILED DESCRIPTION

Figure 1:
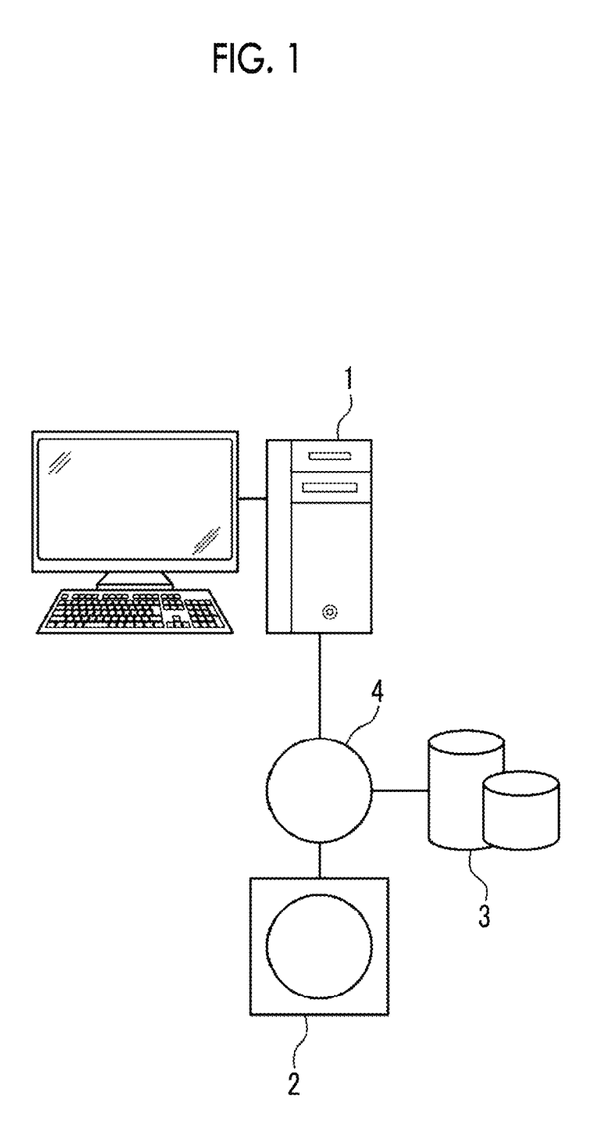
FIG. 1 is a hardware configuration diagram illustrating an outline of a diagnosis support system to which a medical image processing apparatus according to an embodiment of the present disclosure is applied.

Hereinafter, embodiments of the present disclosure will be described in detail with reference to the drawings. FIG. 1 is a hardware configuration diagram illustrating an outline of a diagnosis support system to which a learning device and a medical image processing apparatus according to an embodiment of the present disclosure are applied. As illustrated in FIG. 1, in the diagnosis support system, a learning device and a medical image processing apparatus (hereinafter, referred to as a medical image processing apparatus) 1 according to the present embodiment, a three-dimensional image capturing device 2, and an image storage server 3 are connected via a network 4 in a communicable state.

The three-dimensional image capturing device 2 is a device that images a part as a diagnosis target of a subject to generate a three-dimensional image representing the part, and specifically, is a CT device, an MRI device, a positron emission tomography (PET) device, or the like. The three-dimensional image generated by the three-dimensional image capturing device 2 is transmitted to the image storage server 3 to be saved. In the present embodiment, a diagnosis target part of a patient as the subject is a brain, the three-dimensional image capturing device 2 is a CT device, and a CT image of a head including the brain of the subject is generated as a target image. It is assumed that the learning image used in the training described below is the CT image of the brain, and the disease region in the learning image is labeled to generate a teacher label.

The image storage server 3 is a computer that saves and manages various kinds of data, and comprises a large-capacity external storage device and software for database management. The image storage server 3 performs communication with other devices via the network 4 in a wired or wireless manner, and transmits and receives image data and the like. Specifically, the various kinds of data including the image data of the target image generated by the three-dimensional image capturing device 2 are acquired via the network, and are saved and managed in a recording medium such as a large-capacity external storage device. The image data storage format and the communication between the devices via the network 4 are based on a protocol such as Digital Imaging and Communication in Medicine (DICOM).

The medical image processing apparatus 1 is obtained by installing a learning program and a medical image processing program of the present embodiment in one computer. The computer may be a workstation or a personal computer that a doctor performing a diagnosis operates directly, or a server computer connected to the workstation or personal computer via a network. The learning program and the medical image processing program may be stored in a storage device of the server computer connected to the network or in a network storage in a state of being accessible from the outside, and may be downloaded and installed in a computer in response to a request. The learning program and the medical image processing program are distributed by being recorded on a recording medium such as a digital versatile disc (DVD) or a compact disc read only memory (CD-ROM), and are installed to a computer from the recording medium.

Figure 2:
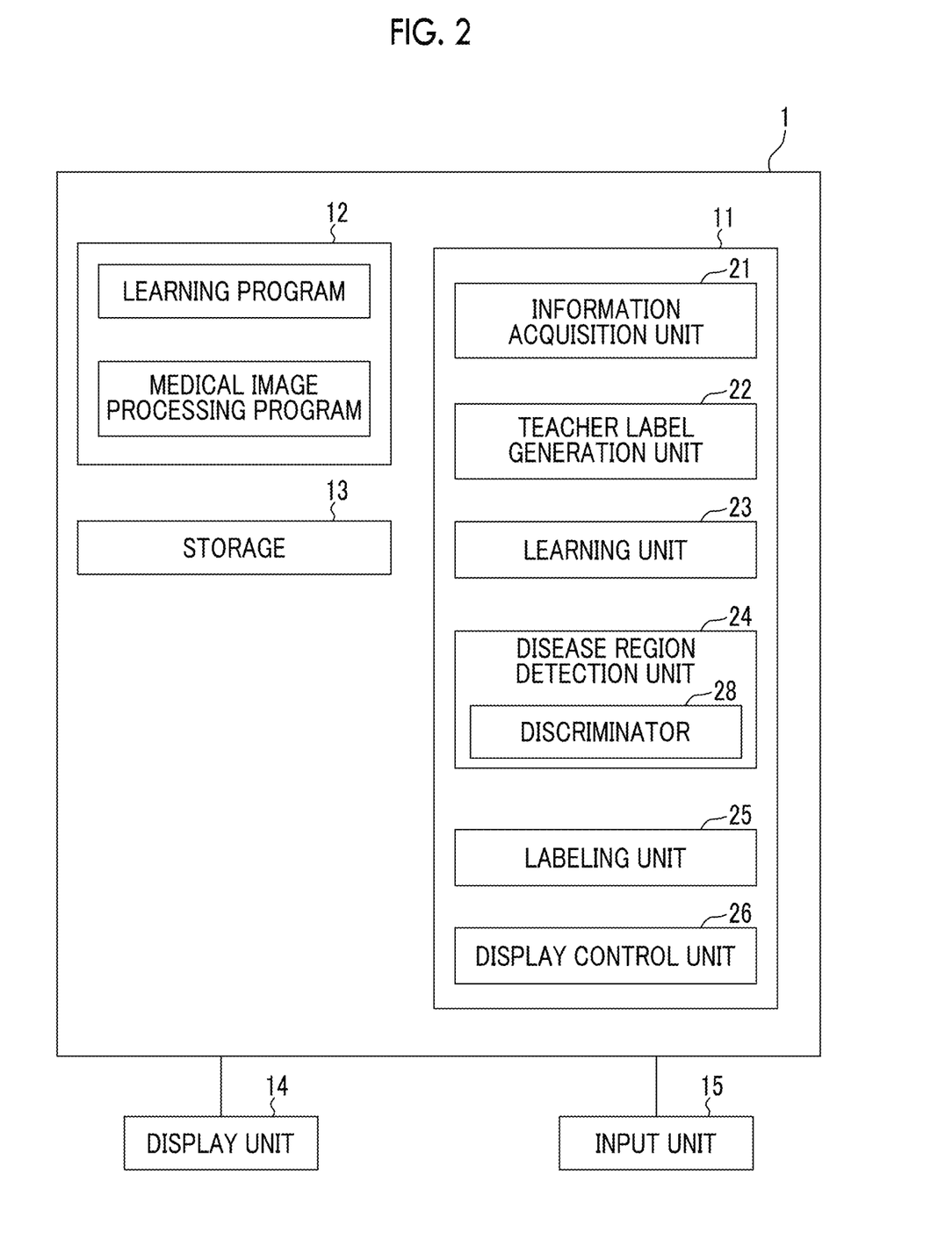
FIG. 2 is a diagram illustrating a schematic configuration of the medical image processing apparatus according to the embodiment of the present disclosure.

FIG. 2 is a diagram illustrating a schematic configuration of the medical image processing apparatus realized by installing the learning program and the medical image processing program on a computer. As illustrated in FIG. 2, the medical image processing apparatus 1 comprises a central processing unit (CPU) 11, a memory 12, and a storage 13 as a standard workstation configuration. In addition, a display unit 14 such as a liquid crystal display, and an input unit 15 such as a keyboard and a mouse are connected to the medical image processing apparatus 1.

The storage 13 consists of a hard disk drive and the like, and various kinds of information including the target image as the processing target acquired from the image storage server 3 via the network 4, the learning image for training a neural network which will be described below, the teacher label for the learning image, and information required for the process are stored.

In the memory 12, the learning program and the medical image processing program are stored. The learning program defines, as processes executed by the CPU 11, an information acquisition process of acquiring a learning image including a disease region and a first teacher label that specifies the disease region included in the learning image, a teacher label generation process of generating at least one second teacher label of which a criterion for specifying the disease region is different from the first teacher label, and a learning process of training the discriminator that detects the disease region included in a target image on the basis of the learning image, the first teacher label, and at least one second teacher label.

The medical image processing program defines, as processes executed by the CPU 11, a disease region detection process of detecting a disease region included in a target image as a target of the detection of the disease region acquired by the information acquisition process, a labeling process of labeling the detected disease region, and a display control process of causing the display unit 14 to display the labeled target image.

With the CPU 11 executing those processes according to the learning program and the medical image processing program, the computer functions as an information acquisition unit 21, a teacher label generation unit 22, a learning unit 23, a disease region detection unit 24, a labeling unit 25, and a display control unit 26.

The information acquisition unit 21 acquires the learning image and the first teacher label that specifies the disease region included in the learning image, from the image storage server 3 via an interface (not illustrated) connected to the network. Further, the target image as the processing target is also acquired. In a case where the learning image, the first teacher label, and the target image are already stored in the storage 13, the information acquisition unit 21 may acquire the learning image, the first teacher label, and the target image from the storage 13.

Figure 3:
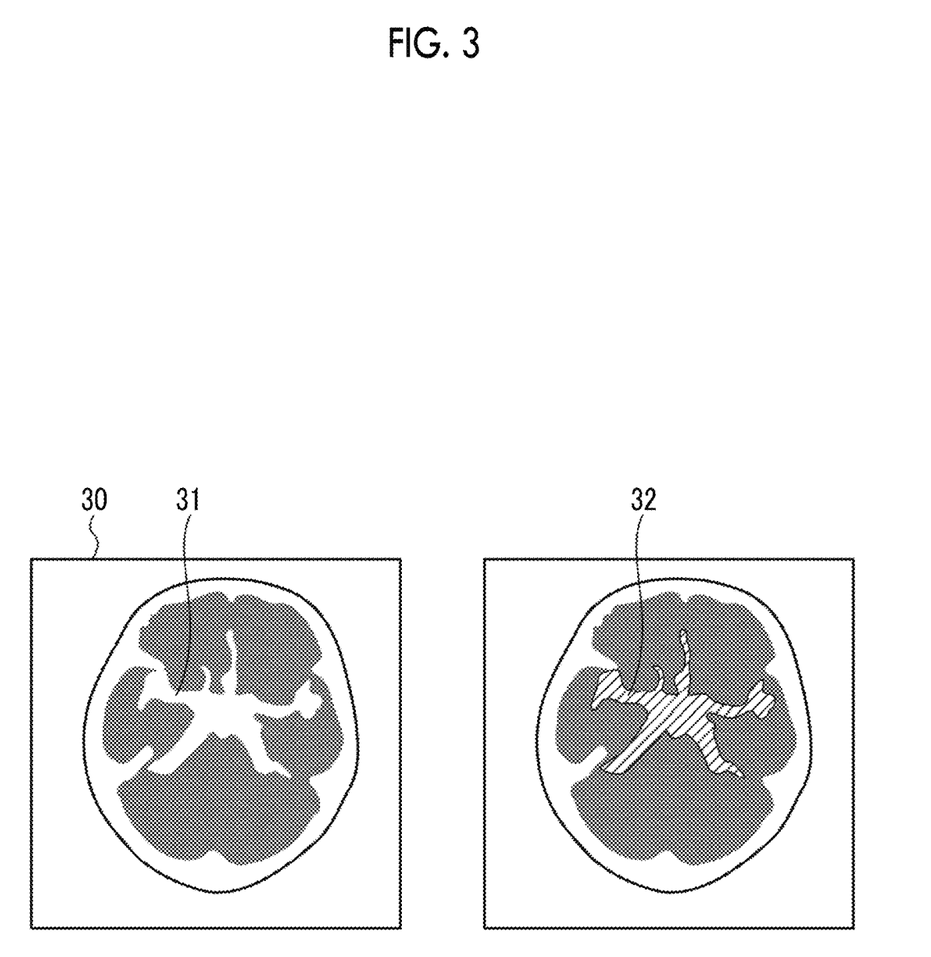
FIG. 3 is a diagram illustrating a brain image and a teacher label.

Here, in the CT image of the brain, the disease region such as the cerebral hemorrhage shows a higher or lower CT value as compared with the surrounding region. For example, in a case of a brain image 30 as illustrated in FIG. 3, a disease region 31 shows a higher CT value as compared with the other region. In such a case, since the contrast between the disease region 31 and the surrounding region is clear, no matter who creates the teacher label, a teacher label 32 substantially matches the disease region 31 in the brain image 30.

Figure 4:
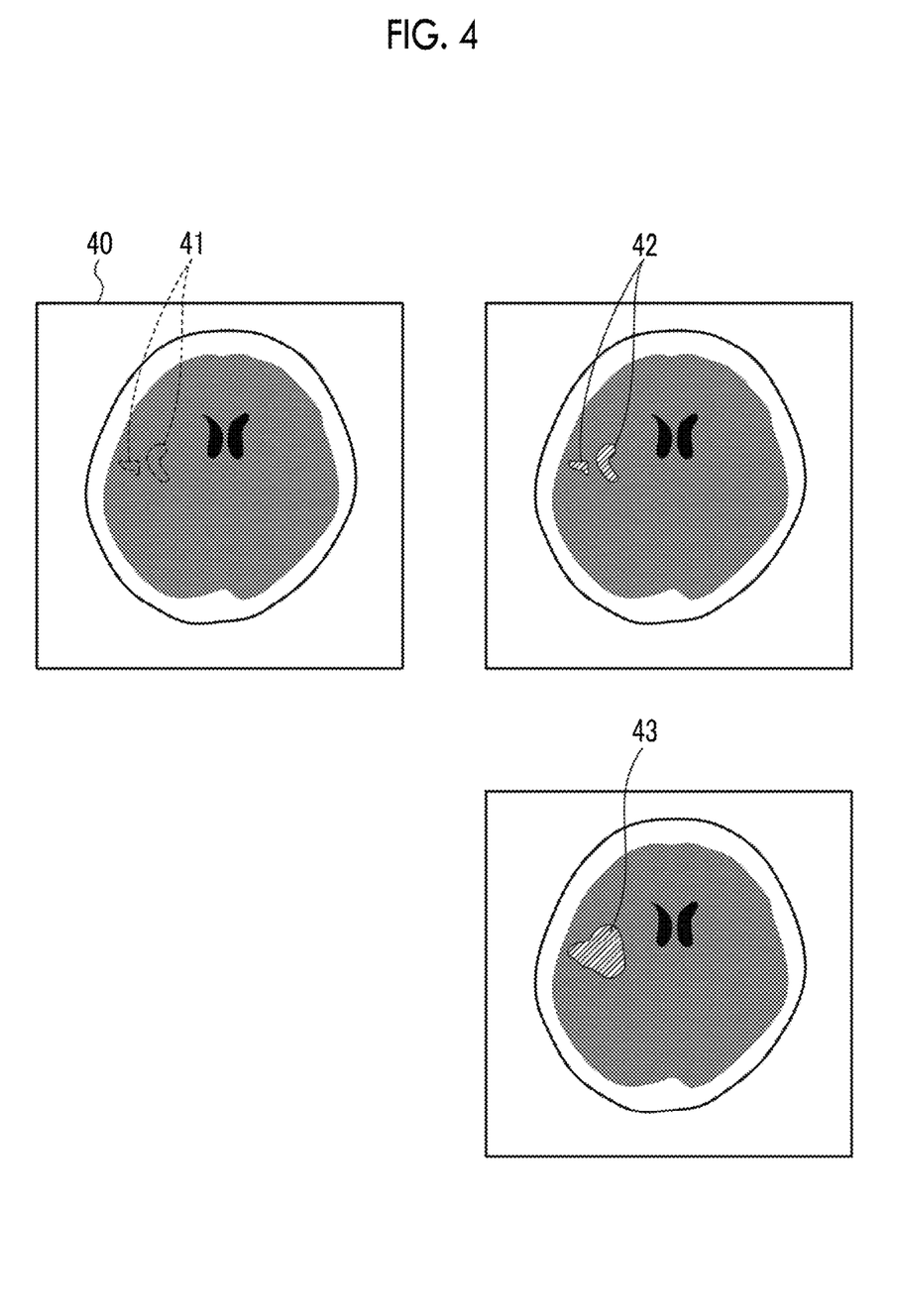
FIG. 4 is a diagram illustrating a brain image and a teacher label.

On the other hand, as in a brain image 40 illustrated in FIG. 4, for a disease such as mild subarachnoid hemorrhage or cerebral infarction in the hyperacute phase, the contrast between a disease region 41 and the surrounding region is unclear in many cases. In FIG. 4, the fact that the contrast is unclear is indicated by a broken line. In such a case, the extent that is regarded as the disease region to be labeled differs depending on the doctor performing the labeling. For example, a certain doctor may assign a teacher label 42 having a small size, while another doctor may assign a teacher label 43 having a large size.

The teacher label generation unit 22 generates at least one second teacher label of which the criterion for specifying the disease region is different from the first teacher label. Therefore, the teacher label generation unit 22 derives a representative value of CT values in a region 55 to which a first teacher label 51 is assigned, in an acquired learning image 50 as illustrated in FIG. 5, and generates a region corresponding to the first teacher label 51 and a region in which CT values of a region adjacent to the region in the first teacher label 51 in the learning image 50 are within a predetermined range with respect to the representative value, as the second teacher label.

In the present embodiment, the teacher label generation unit 22 derives an average value $\mu$ of the CT values in the region 55 as the representative value, but the disclosure is not limited thereto. A median, a weighted average value, a maximum value, a minimum value, or the like may be used as the representative value. In the present embodiment, the teacher label generation unit 22 derives a standard deviation $\sigma$ of the CT values in the region 55 and a centroid position 56 of the region specified by the first teacher label 51 in the learning image 50.

Figure 5:
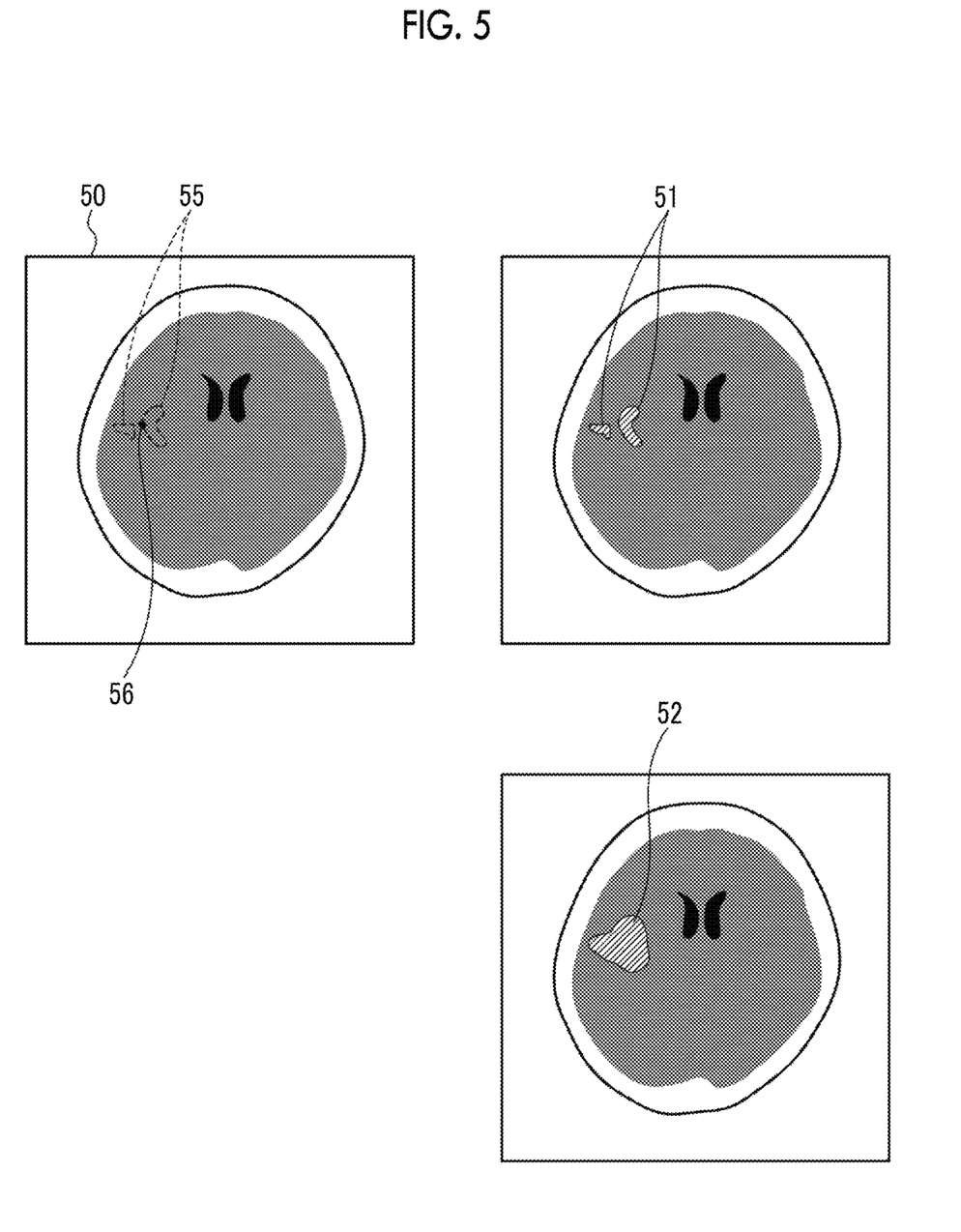
FIG. 5 is a diagram illustrating a learning image, a first teacher label, and a second teacher label.
Figure 6:
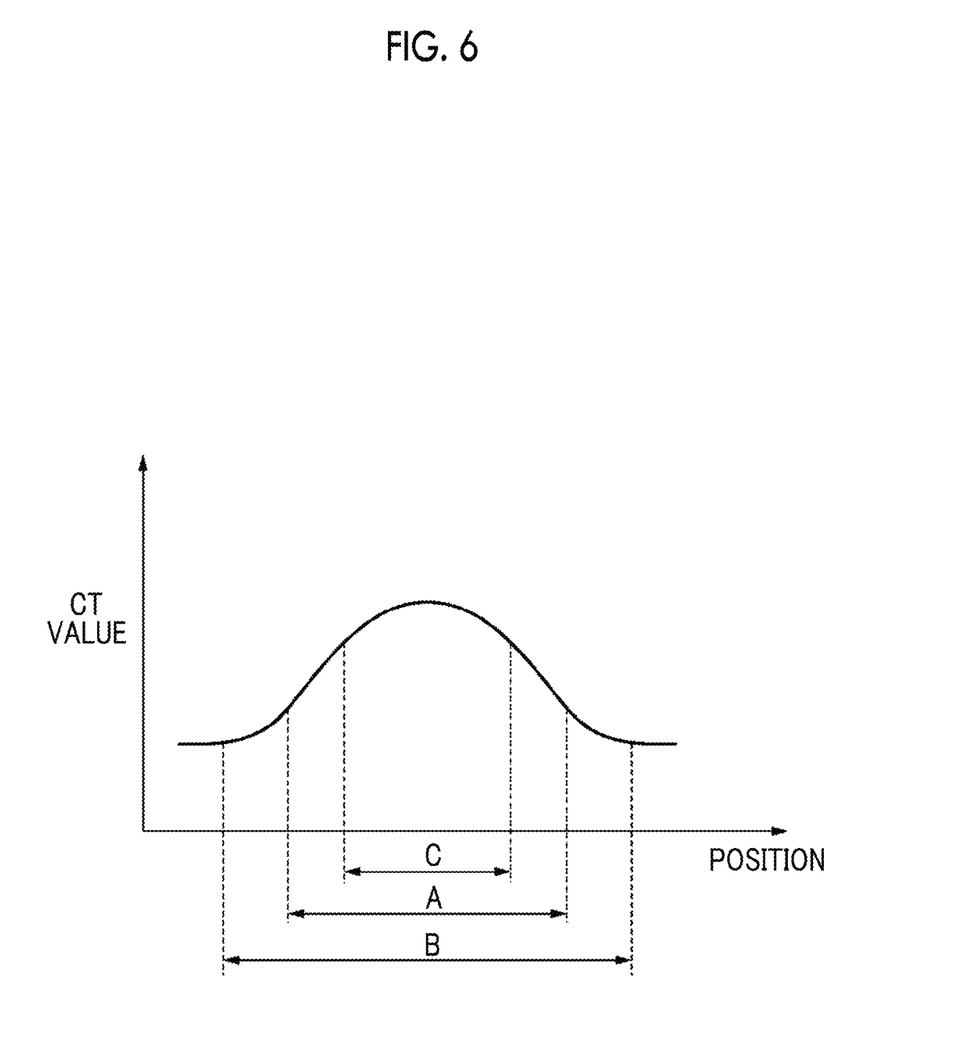
FIG. 6 is a diagram illustrating a distribution of CT values in a disease region.

The teacher label generation unit 22 generates a second teacher label 52 as illustrated in FIG. 5 by labeling a region consisting of pixels having CT values in a range of $\mu \pm \sigma$ among pixels in a predetermined distance from the centroid position 56 in the learning image 50. Here, FIG. 6 is a diagram illustrating a distribution of CT values in a disease region. As illustrated in FIG. 6, the CT value of the disease region is a higher value as compared with the CT value of the surrounding region, and the CT value becomes smaller toward the vicinity of the disease region, and is distributed to gradually match the CT value of the region around the disease region. Therefore, in a case where the first teacher label is assigned to a range indicated by an arrow A illustrated in FIG. 6, the second teacher label 52 having a size larger than the first teacher label 51 can be generated as indicated by an arrow B by labeling a region consisting of pixels having CT values of $\mu-\sigma$. On the other hand, the second teacher label 52 having a size smaller than the first teacher label 51 can be generated as indicated by an arrow C by labeling a region consisting of pixels having CT values of $\mu+\sigma$.

In a case where the boundary of the disease region in the learning image 50 is unclear, the second teacher label 52 different from the first teacher label 51 is generated as illustrated in FIG. 5. On the other hand, in a case where the boundary of the disease region is clear as illustrated in FIG. 3, since the CT value in the disease region is constant, and standard deviation $\sigma$ is substantially zero. In such a case, the second teacher label 52 generated by the teacher label generation unit 22 is substantially the same as the first teacher label 51.

In the present embodiment, one second teacher label 52 is generated from the first teacher label 51, but a plurality of second teacher labels may be generated. In this case, for example, a plurality of second teacher labels 52 may be generated by labeling a region consisting of pixels having CT values of each of $\mu\pm0.5\sigma$, $\mu\pm\sigma$, $\mu\pm1.5\sigma$, and the like.

The learning unit 23 trains a discriminator 28 that detects the disease region included in the target image, on the basis of the learning image 50, the first teacher label 51, and the second teacher label 52. The discriminator 28 discriminates the disease region of the brain included in the target image. In the present embodiment, it is assumed that the discriminator 28 is a convolutional neural network (hereinafter, referred to as CNN) which is one of multi-layer neural networks in which a plurality of processing layers are hierarchically connected to each other and deep learning is performed.

The convolutional neural network consists of a plurality of convolutional layers and pooling layers. The convolutional layer performs a convolution process using various kernels on the input images, and outputs a feature map consisting of feature quantity data obtained by the convolution process. The kernel has an n×n pixel size (for example, n=3), and a weight is set in each element. Specifically, a weight such as a differential filter for emphasizing the edge of the input image is set. The convolutional layer applies the kernel to the entire feature map output from the input image or the processing layer at the former stage while shifting the attention pixel of the kernel. Further, the convolutional layer applies an activation function such as a sigmoid function to the convolved value to output the feature map.

The pooling layer reduces the amount of data of the feature map by pooling the feature map output by the convolutional layer, and outputs the feature map of which the amount of data is reduced.

Figure 7:
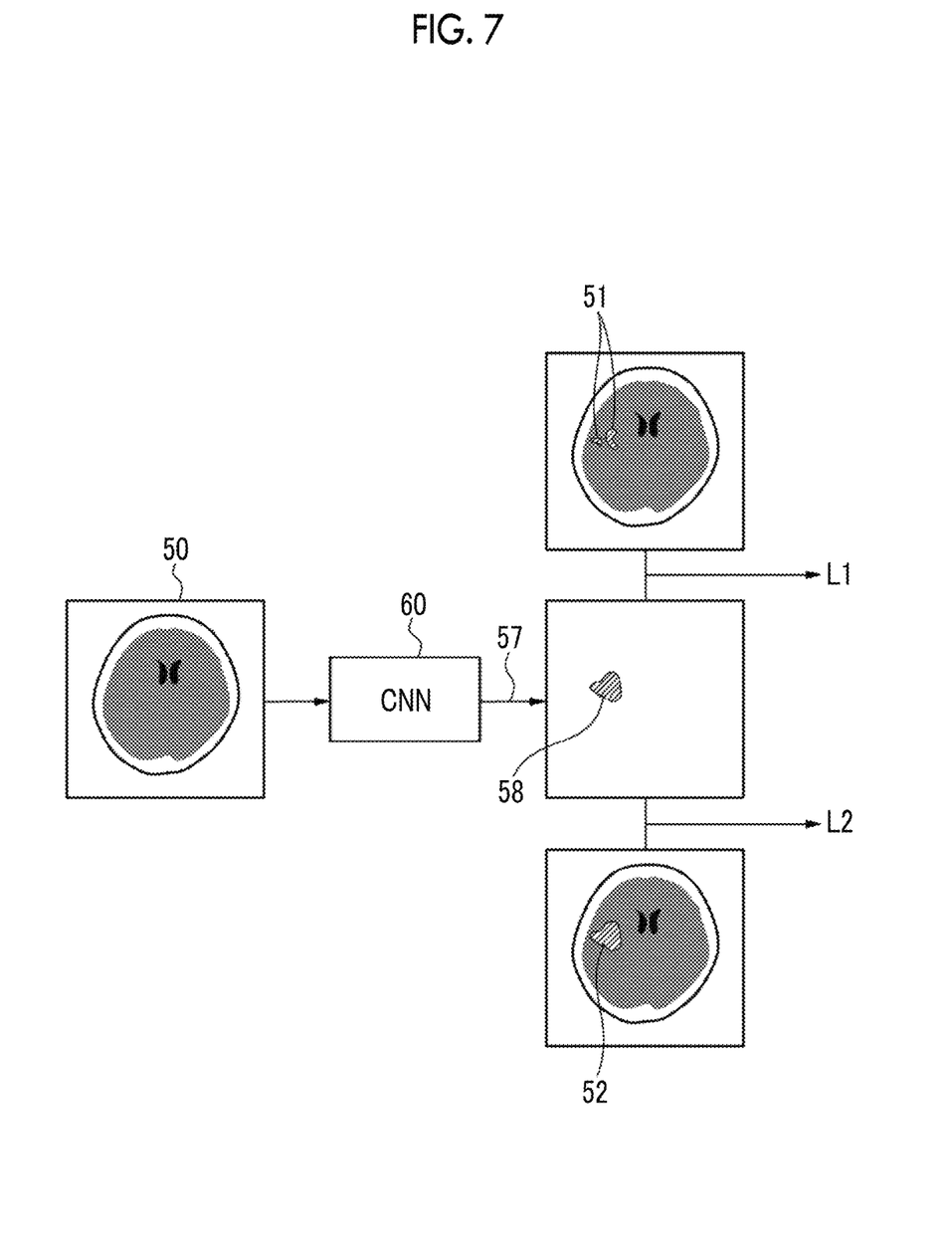
FIG. 7 is a conceptual diagram of learning in the present embodiment.

FIG. 7 is a conceptual diagram of learning in the present embodiment. As illustrated in FIG. 7, the learning unit 23 inputs the learning image 50 to a CNN 60 as the discriminator 28, and outputs a discrimination result 57 of the disease region in the learning image 50 from the CNN 60. The discrimination result 57 represents the probability that each pixel of the learning image 50 is the disease region. The learning unit 23 specifies the region consisting of pixels of which the probability is equal to or greater than a predetermined threshold value, as a learning disease region 58. Then, the learning unit 23 derives a first loss L1 on the basis of the difference between first teacher label 51 and the discrimination result 57 of the learning disease region 58. The first loss L1 is a difference between the probability and the threshold value for the pixel which is discriminated not to be the disease region even though the pixel is the disease region in the first teacher label 51, and a difference between the threshold value and the probability for the pixel which is discriminated to be the disease region even though the pixel is not the disease region in the first teacher label 51.

The learning unit 23 derives a second loss L2 on the basis of the difference between the second teacher label 52 and the discrimination result 57. The second loss L2 is a difference between the probability and the threshold value for the pixel which is discriminated not to be the disease region even though the pixel is the disease region in the second teacher label 52, and a difference between the threshold value and the probability for the pixel which is discriminated to be the disease region even though the pixel is not the disease region in the second teacher label 52.

Further, the learning unit 23 derives a total loss L0 for each pixel of the learning image 50 by weighing and adding the first loss L1 and the second loss L2 as illustrated in the following Equation (1). α in Equation (1) is a weight coefficient, and is a value of 0.5, for example, but the disclosure is not limited thereto.

$$L0=L1+\alpha \cdot L2 \qquad (1)$$

The learning unit 23 trains the CNN 60, that is, the discriminator 28 using a large number of learning images 50, first teacher labels 51, and second teacher labels 52 such that the total loss L0 is equal to or less than the predetermined threshold value. Specifically, the learning unit 23 trains the CNN 60, that is, the discriminator 28 by deriving the number of convolutional layers, the number of pooling layers, the kernel coefficient and the kernel size in the convolutional layer, and the like which constitute the CNN 60 such that the total loss L0 is equal to or less than the predetermined threshold value. As a result, in a case where the target image is input to the trained discriminator 28, the discriminator 28 outputs the probability that each pixel of the target image is the disease region of the brain. The learning unit 23 may perform training a predetermined number of times instead of performing training such that the total loss L0 is equal to or less than the predetermined threshold value.

The learning unit 23 trains the CNN 60, that is, the discriminator 28, so that a trained model that outputs, as the discrimination result, the probability that the pixel is the disease region included in the target image in a case where the target image is input is constructed. The trained model is applied to the disease region detection unit as the discriminator 28.

In a case where the target image is input, the disease region detection unit 24 detects the disease region included in the target image using the discriminator 28. That is, in a case where the target image is input to the discriminator 28, the disease region detection unit 24 outputs the probability that each pixel of the target image is the disease region of the brain from the discriminator 28. Then, the disease region detection unit 24 detects the pixel of which the probability exceeds the predetermined threshold value, as the pixel of the disease region included in the target image.

Figure 8:
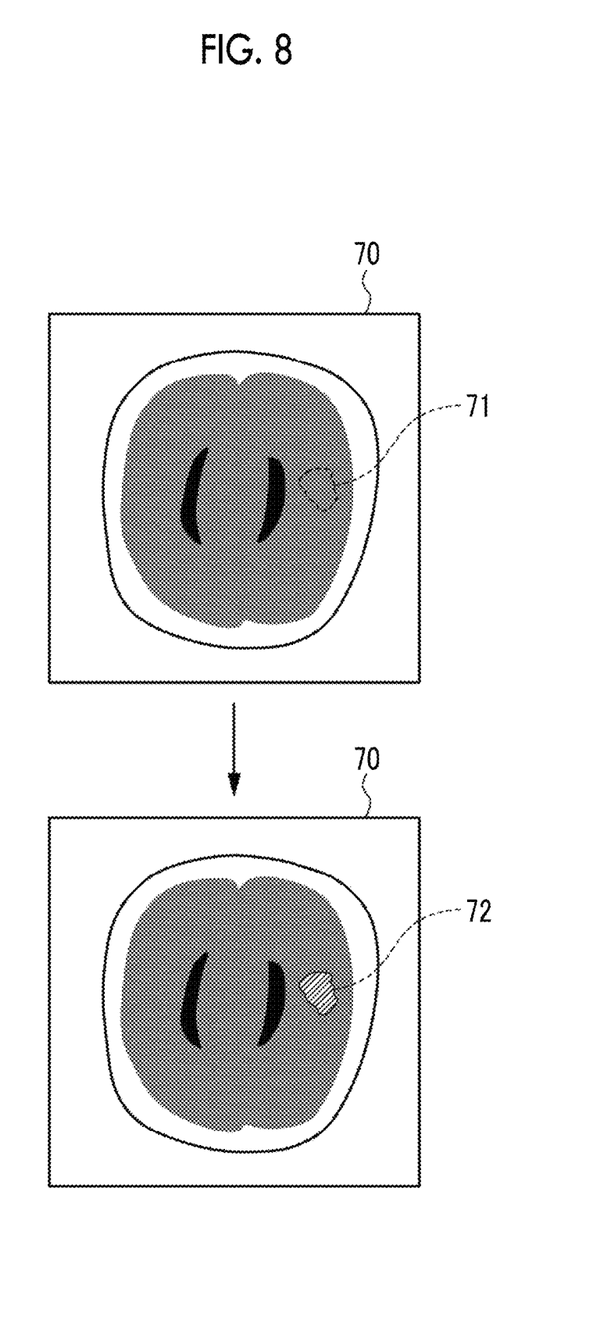
FIG. 8 is a diagram for describing detection of a disease region from a target image.

The labeling unit 25 performs labeling of the disease region included in the target image on the basis of the detection result by the disease region detection unit 24. For example, in a case where a target image 70 including a disease region 71 (indicated by a broken line) is input to the disease region detection unit 24 as illustrated in FIG. 8, the disease region detection unit 24 detects the disease region 71 included in the target image 70. The labeling unit 25 performs labeling by assigning a label to the disease region 71 included in the target image 70. For example, as illustrated in FIG. 8, labeling is performed by assigning a label 72 to the disease region 71 by changing the color of the disease region. In FIG. 8, changing the color is illustrated by adding hatching. Further, the labeling may be performed by adding a frame surrounding the disease region.

The display control unit 26 causes the display unit 14 to display the labeled target image.

Figure 9:
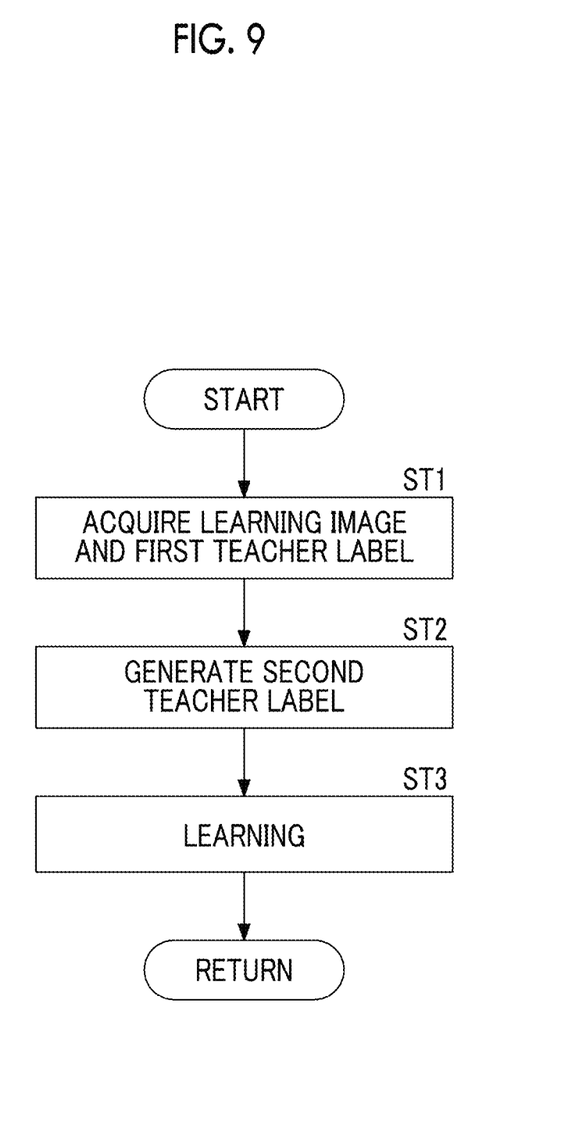
FIG. 9 is a flowchart illustrating a learning process performed in the present embodiment.

Next, the process performed in the present embodiment will be described. FIG. 9 is a flowchart illustrating a learning process performed in the present embodiment. The plurality of learning images and first teacher labels are acquired by the information acquisition unit 21 from the image storage server 3, and are saved in the storage 13. First, the information acquisition unit 21 acquires one set of the learning image 50 and the first teacher label 51 from the plurality of learning images and first teacher labels saved in the storage 13 (Step ST1). Next, the teacher label generation unit 22 generates at least one second teacher label 52 of which the criterion for specifying the disease region is different from the first teacher label 51 (Step ST2).

Then, the learning unit 23 inputs the learning image 50, the first teacher label 51, and the second teacher label 52 to the CNN 60 to derive the total loss L0, and trains the CNN 60, that is, the discriminator 28 such that the total loss L0 is equal to or less than the predetermined threshold value (Step ST3).

Then, the process returns to Step ST1 so that the next learning image 50 and first teacher label 51 are acquired from the storage 13, and the processes of Step ST2 and Step ST3 are repeated. As a result, the trained discriminator 28 is constructed.

Figure 10:
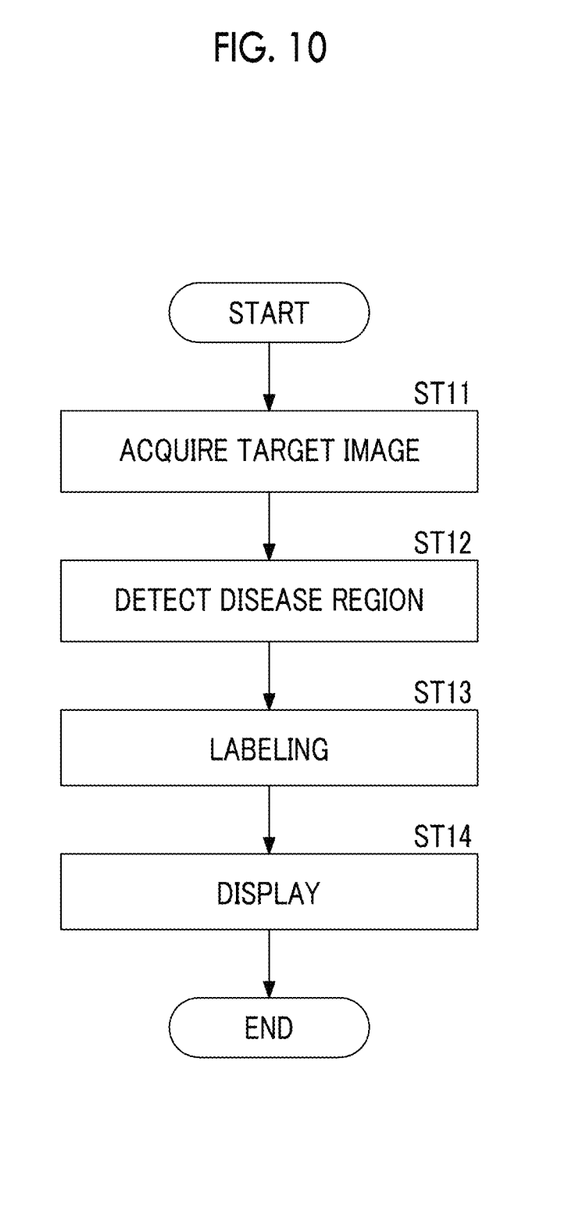
FIG. 10 is a flowchart illustrating a medical image process performed in the present embodiment.

Next, a medical image process of detecting the disease region performed in the present embodiment will be described. FIG. 10 is a flowchart illustrating the medical image process performed in the present embodiment. The information acquisition unit 21 acquires the target image (Step ST11), and the disease region detection unit 24 detects the disease region included in the target image (Step ST12). Next, the labeling unit 25 performs labeling of the disease region detected from the target image 70 (Step ST13). Then, the display control unit 26 causes the display unit 14 to display the labeled target image (Step ST14), and the process is ended.

In this manner, in the present embodiment, the learning image 50 including the disease region and the first teacher label 51 that specifies the disease region included in the learning image 50 are acquired, and at least one second teacher label 52 of which the criterion for specifying the disease region is different from the first teacher label 51 is generated. The discriminator 28 that detects the disease region included in the target image 70 is trained on the basis of the learning image 50, the first teacher label 51, and at least one second teacher label 52. Therefore, the discriminator 28 detects the disease region from the target image on the basis of not only the criterion of the first teacher label 51 but also the criterion of the second teacher label 52. As a result, in the present embodiment, since the discriminator 28 is trained using a plurality of teacher labels with different criteria, the disease region in which the determination is likely to differ depending on the doctor and the contrast with the surrounding region is unclear can be detected by the trained discriminator 28 with a certain allowable range. Therefore, the second teacher label 52 is generated such that the disease in a range larger than the first teacher label 51 is labeled, and therefore the discriminator 28 can be constructed to detect a wide range of disease region as compared with a case where training is performed using only the first teacher label 51. Accordingly, according to the present embodiment, it is possible to prevent the overlooking of the disease region included in the target image.

Figure 11:
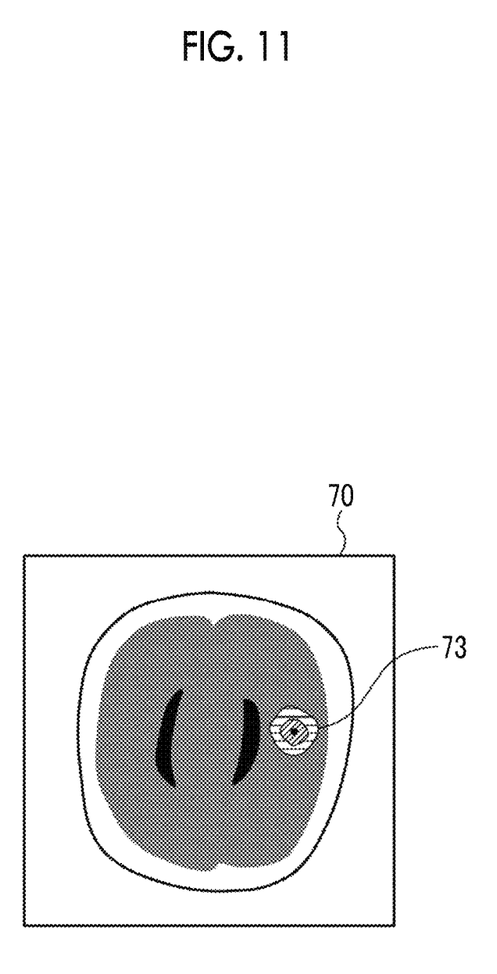
FIG. 11 is a diagram for describing detection of a disease region from a target image.

In the above-described embodiment, the probability representing the disease region, which is output by the discriminator 28 of the disease region detection unit 24, becomes smaller toward the vicinity of the disease region. Therefore, as illustrated in FIG. 11, labels with different transparency may be assigned in stages according to the probability output by the discriminator 28. In FIG. 11, different hatching illustrates that the transparency is different. Not only the color may be changed in stages, but also the transparency may be changed gradually. Further, instead of the transparency, the color may be changed.

In the above-described embodiment, as illustrated in FIG. 3, in a case of the learning image 50 in which the boundary of the disease region is clear, since the CT value in the disease region is constant, the standard deviation σ is substantially zero. In such a case, the second teacher label 52 generated by the teacher label generation unit 22 is substantially the same as the first teacher label 51. Therefore, in a case of the learning image 50 in which the boundary of the disease region is clear, the second teacher label 52 may not be generated. For example, in the teacher label generation unit 22, it is determined whether the standard deviation σ of the CT value in the disease region is equal to or less than the predetermined threshold value, and in a case where it is determined that the standard deviation σ is equal to or less than the threshold value, the second teacher label 52 may not be generated. In this case, the discriminator 28 is trained using only the first teacher label 51, and the first loss L1 is used as the total loss L0.

In the above-described embodiment, the second teacher label 52 having a size larger than the first teacher label 51 is generated, but the second teacher label 52 having a size smaller than the first teacher label 51 may be generated.

In the above-described embodiment, the teacher label generation unit 22 generates the second teacher label 52 from the first teacher label 51, but the disclosure is not limited thereto. For example, the second teacher label 52 may be generated from the learning image 50.

In the above-described embodiment, the target image is a three-dimensional image including the brain, and the disease region of the brain is detected, but the disclosure is not limited thereto. Even in a case where the disease region included in other structures such as a lung, a liver, a heart, or a kidney other than the brain is detected, the technique of the present disclosure can be applied. For example, by using the medical image including the liver as the learning image, and using the first teacher label obtained by labeling the mass of the liver, the discriminator 28 that can detect the mass included in the liver without overlooking the mass can be constructed. Further, by using the medical image including the lung as the learning image, and using the first teacher label obtained by labeling a lung nodule, the discriminator 28 that can detect the lung nodule included in the lung without overlooking the lung nodule can be constructed.

Further, in the above-described embodiment, a three-dimensional medical image is used as the target image, but the disclosure is not limited thereto. Each of tomographic images constituting the three-dimensional medical image may be used as the target image. Further, a two-dimensional X-ray image acquired by projectional radiography may be used as the target image. In this case, the learning image and the first teacher label are prepared according to the type of the target image, and the training of the CNN 60, that is, the discriminator 28 is performed.

Further, in the above-described embodiment, the CNN 60 is used as the discriminator 28, but the disclosure is not limited thereto. As long as the neural network includes a plurality of processing layers, a deep neural network (DNN), a recurrent neural network (RNN), or the like can be used.

In the above-described embodiment, for example, the following various processors can be used as the hardware structure of processing units executing various processes such as the information acquisition unit 21, the teacher label generation unit 22, the learning unit 23, the disease region detection unit 24, the labeling unit 25, and the display control unit 26. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (programs) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor fulfilling the functions of the entire system including a plurality of processing units by means of one integrated circuit (IC) chip as typified by a system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

What is claimed is:

1. A learning device comprising at least one processor, wherein the processor is configured to:
    acquire a learning image including a disease region and a first teacher label that specifies the disease region included in the learning image;
    generate at least one second teacher label of which a criterion for specifying the disease region is different from the first teacher label on the basis of a standard deviation of a signal value of a region in the first teacher label; and
    train a discriminator that detects a disease region included in a target image on the basis of the learning image, the first teacher label, and the at least one second teacher label, wherein the first teacher label and the second teacher label are respectively inputted to the discriminator for training.

2. The learning device according to claim 1, wherein the generation of the at least one second teacher label is further on the basis of a centroid position of the first teacher label in the learning image.

3. The learning device according to claim 2, wherein the processor is configured to derive a representative value of the signal values in the region of the first teacher label in the learning image, and generates a region corresponding to the first teacher label and a region in which signal values of a region adjacent to the region in the first teacher label in the learning image are within a predetermined range with respect to the representative value, as the second teacher label.

4. The learning device according to claim 1, wherein the processor is configured to train the discriminator by inputting the learning image to the discriminator to detect a learning disease region, deriving a first loss between the learning disease region and the first teacher label and a second loss between the learning disease region and the second teacher label, deriving a total loss from the first loss and the second loss, and using the total loss in training the discriminator.

5. The learning device according to claim 1, wherein the processor is configured to acquire an image of a brain, and the disease region is a region of a brain disease.

6. A medical image processing apparatus comprising at least one processor to which the discriminator trained by the learning device according to claim 1 is applied, wherein the processor is configured to detect a disease region included in a target medical image in a case where the target medical image is input.

7. The medical image processing apparatus according to claim 6, wherein the processor is further configured to:
    perform labeling of the disease region detected from the target medical image; and
    cause a display to display the labeled target medical image.

8. A discriminator which is trained by the learning device according to claim 1, and which detects a disease region included in a target medical image in a case where the target medical image is input.

9. A learning method comprising:
    acquiring a learning image including a disease region and a first teacher label that specifies the disease region included in the learning image;
    generating at least one second teacher label of which a criterion for specifying the disease region is different from the first teacher label on the basis of a standard deviation of a signal value of a region in the first teacher label; and
    training a discriminator that detects a disease region included in a target image on the basis of the learning image, the first teacher label, and the at least one second teacher label, wherein the first teacher label and the second teacher label are respectively inputted to the discriminator for training.

10. A medical image processing method of detecting a disease region included in a target medical image in a case where the target medical image is input, using the discriminator trained by the learning method according to claim 9.

11. A non-transitory computer-readable storage medium that stores a learning program causing a computer to execute:
- a procedure of acquiring a learning image including a disease region and a first teacher label that specifies the disease region included in the learning image;
- a procedure of generating at least one second teacher label of which a criterion for specifying the disease region is different from the first teacher label on the basis of a standard deviation of a signal value of a region in the first teacher label; and
- a procedure of training a discriminator that detects a disease region included in a target image on the basis of the learning image, the first teacher label, and the at least one second teacher label, wherein the first teacher label and the second teacher label are respectively inputted to the discriminator for training.

12. A non-transitory computer-readable medium, storing a medical image processing program causing a computer to execute a procedure of detecting a disease region included in a target medical image in a case where the target medical image is input, using the discriminator trained by the learning method according to claim 9.

* * * * *